United States Patent
Celentano et al.

(10) Patent No.: US 8,361,291 B2
(45) Date of Patent: Jan. 29, 2013

(54) SYSTEM AND METHOD FOR QUALITY ASSURANCE OF A BIOSENSOR TEST STRIP

(75) Inventors: Michael J. Celentano, Fishers, IN (US); Henning Groll, Indianapolis, IN (US); James L. Pauley, Fishers, IN (US); Steven K. Moore, Carmel, IN (US)

(73) Assignees: Roche Diagnostics Operations, Inc., Indianapolis, IN (US); Roche Operations Ltd., Hamilton (BM)

( * ) Notice: Subject to any disclaimer, the term of this patent is extended or adjusted under 35 U.S.C. 154(b) by 0 days.

(21) Appl. No.: 13/342,268

(22) Filed: Jan. 3, 2012

(65) Prior Publication Data

US 2012/0097536 A1   Apr. 26, 2012

Related U.S. Application Data

(62) Division of application No. 12/484,603, filed on Jun. 15, 2009, now Pat. No. 8,092,668, which is a division of application No. 10/961,352, filed on Oct. 8, 2004, now Pat. No. 7,569,126.

(60) Provisional application No. 60/581,002, filed on Jun. 18, 2004.

(51) Int. Cl.
*G01N 27/416* (2006.01)
*G01N 27/327* (2006.01)

(52) U.S. Cl. .................................. 204/401; 204/403.02

(58) Field of Classification Search .................. 204/400; 205/775, 778, 777.5, 792
See application file for complete search history.

(56) References Cited

U.S. PATENT DOCUMENTS 7,540,947 B2 * 6/2009 Ueno et al. ............... 204/403.01

FOREIGN PATENT DOCUMENTS

WO   WO 2004/005908 A1 *  1/2004

* cited by examiner

*Primary Examiner* — Alex Noguerola
(74) *Attorney, Agent, or Firm* — Woodard, Emhardt, Moriarty, McNett & Henry LLP

(57) ABSTRACT

The present invention provides a test strip for measuring a signal of interest in a biological fluid when the test strip is mated to an appropriate test meter, wherein the test strip and the test meter include structures to verify the integrity of the test strip traces, to measure the parasitic resistance of the test strip traces, and to provide compensation in the voltage applied to the test strip to account for parasitic resistive losses in the test strip traces.

4 Claims, 8 Drawing Sheets

SYSTEM AND METHOD FOR QUALITY ASSURANCE OF A BIOSENSOR TEST STRIP

REFERENCE TO RELATED APPLICATIONS

This application is a divisional of application Ser. No. 12/484,603, filed Jun. 15, 2009, now U.S. Pat No. 8,092,668 which is a divisional of application Ser. No. 10/961,352, filed Oct. 8, 2004, now U.S. Pat. No. 7,569,126, which claims the benefit of U.S. Provisional Application No. 60/581,002, filed Jun. 18, 2004, and which are incorporated herein by reference in their entirety.

TECHNICAL FIELD OF THE INVENTION

The present invention relates to an apparatus for use in measuring signals such as those related to concentrations of an analyte (such as blood glucose) in a biological fluid as well as those related to interferants (such as hematocrit and temperature in the case of blood glucose) to analyte concentration signals. The invention relates more particularly to a system and method for quality assurance of a biosensor test strip.

BACKGROUND OF THE INVENTION

Measuring the concentration of substances in biological fluids is an important tool for the diagnosis and treatment of many medical conditions. For example, the measurement of glucose in body fluids, such as blood, is crucial to the effective treatment of diabetes.

Diabetic therapy typically involves two types of insulin treatment: basal, and meal-time. Basal insulin refers to continuous, e.g. time-released insulin, often taken before bed. Meal-time insulin treatment provides additional doses of faster acting insulin to regulate fluctuations in blood glucose caused by a variety of factors, including the metabolization of sugars and carbohydrates. Proper regulation of blood glucose fluctuations requires accurate measurement of the concentration of glucose in the blood. Failure to do so can produce extreme complications, including blindness and loss of circulation in the extremities, which can ultimately deprive the diabetic of use of his or her fingers, hands, feet, etc.

Multiple methods are known for determining the concentration of analytes in a blood sample, such as, for example, glucose. Such methods typically fall into one of two categories: optical methods and electrochemical methods. Optical methods generally involve spectroscopy to observe the spectrum shift in the fluid caused by concentration of the analyte, typically in conjunction with a reagent that produces a known color when combined with the analyte. Electrochemical methods generally rely upon the correlation between a current (Amperometry), a potential (Potentiometry) or accumulated charge (Coulometry) and the concentration of the analyte, typically in conjunction with a reagent that produces charge-carriers when combined with the analyte. See, for example, U.S. Pat. Nos. 4,233,029 to Columbus, 4,225,410 to Pace, 4,323,536 to Columbus, 4,008,448 to Muggli, 4,654, 197 to Lilja et al., 5,108,564 to Szuminsky et al., 5,120,420 to Nankai et al., 5,128,015 to Szuminsky et al., 5,243,516 to White, 5,437,999 to Diebold et al., 5,288,636 to Pollmann et al., 5,628,890 to Carter et al., 5,682,884 to Hill et al., 5,727, 548 to Hill et al., 5,997,817 to Crismore et al., 6,004,441 to Fujiwara et al., 4,919,770 to Priedel, et al., and 6,054,039 to Shieh, which are hereby incorporated in their entireties. The biosensor for conducting the tests is typically a disposable test strip having a reagent thereon that chemically reacts with the analyte of interest in the biological fluid. The test strip is mated to a nondisposable test meter such that the test meter can measure the reaction between the analyte and the reagent in order to determine and display the concentration of the analyte to the user.

FIG. 1 schematically illustrates a typical prior art disposable biosensor test strip, indicated generally at 10 (see, for example, U.S. Pat. Nos. 4,999,582 and 5,438,271, assigned to the same assignee as the present application, and incorporated herein by reference). The test strip 10 is formed on a nonconductive substrate 12, onto which are formed conductive areas 14,16. A chemical reagent 18 is applied over the conductive areas 14,16 at one end of the test strip 10. The reagent 18 will react with the analyte of interest in the biological sample in a way that can be detected when a voltage potential is applied between the measurement electrodes 14a and 16a.

The test strip 10 therefore has a reaction zone 20 containing the measurement electrodes 14a,16a that comes into direct contact with a sample that contains an analyte for which the concentration in the sample is to be determined. In an amperometric or coulometric electrochemical measurement system, the measurement electrodes 14a,16a in the reaction zone 20 are coupled to electronic circuitry (typically in a test meter (not shown) into which the test strip 10 is inserted, as is well known in the art) that supplies an electrical potential to the measurement electrodes and measures the response of the electrochemical sensor to this potential (e.g. current, impedance, charge, etc.). This response is proportional to the analyte concentration.

The test meter contacts the test strip 10 at contact pads 14b,16b in a contact zone 22 of the test strip 10. Contact zone 22 is located somewhat remotely from measurement zone 20, usually (but not always) at an opposite end of the test strip 10. Conductive traces 14c,16c couple the contact pads 14b,16b in the contact zone 22 to the respective measurement electrodes 14a,16a in the reaction zone 20.

Especially for biosensors 10 in which the electrodes, traces and contact pads are comprised of electrically conductive thin films (for instance, noble metals, carbon ink, and silver paste, as non-limiting examples), the resistivity of the conductive traces 14c,16c that connect the contact zone 22 to the reaction zone 20 can amount to several hundred Ohms or more. This parasitic resistance causes a potential drop along the length of the traces 14c,16c, such that the potential presented to the measurement electrodes 14a,16a in the reaction zone 20 is considerably less than the potential applied by the test meter to the contact pads 14b,16b of the test strip 10 in the contact zone 22. Because the impedance of the reaction taking place within the reaction zone 20 can be within an order of magnitude of the parasitic resistance of the traces 14c,16c, the signal being measured can have a significant offset due to the I-R (current×resistance) drop induced by the traces. If this offset varies from test strip to test strip, then noise is added to the measurement result. Furthermore, physical damage to the test strip 10, such as abrasion, cracks, scratches, chemical degradation, etc. can occur during manufacturing, shipping, storage and/or user mishandling. These defects can damage the conductive areas 14,16 to the point that they present an extremely high resistance or even an open circuit. Such increases in the trace resistance can prevent the test meter from performing an accurate test.

Thus, a system and method are needed that will allow for confirmation of the integrity of test strip traces, for measurement of the parasitic resistance of test strip traces, and for controlling the potential level actually applied to the test strip measurement electrodes in the reaction zone. The present invention is directed toward meeting these needs.

SUMMARY OF THE INVENTION

The present invention provides a test strip for measuring a signal of interest in a biological fluid when the test strip is mated to an appropriate test meter, wherein the test strip and the test meter include structures to verify the integrity of the test strip traces, to measure the parasitic resistance of the test strip traces, and to provide compensation in the voltage applied to the test strip to account for parasitic resistive losses in the test strip traces.

BRIEF DESCRIPTION OF THE DRAWINGS

The invention will be further described, by way of example only, with reference to the accompanying drawings, in which.

DETAILED DESCRIPTION OF THE PREFERRED EMBODIMENTS

Figure 1:
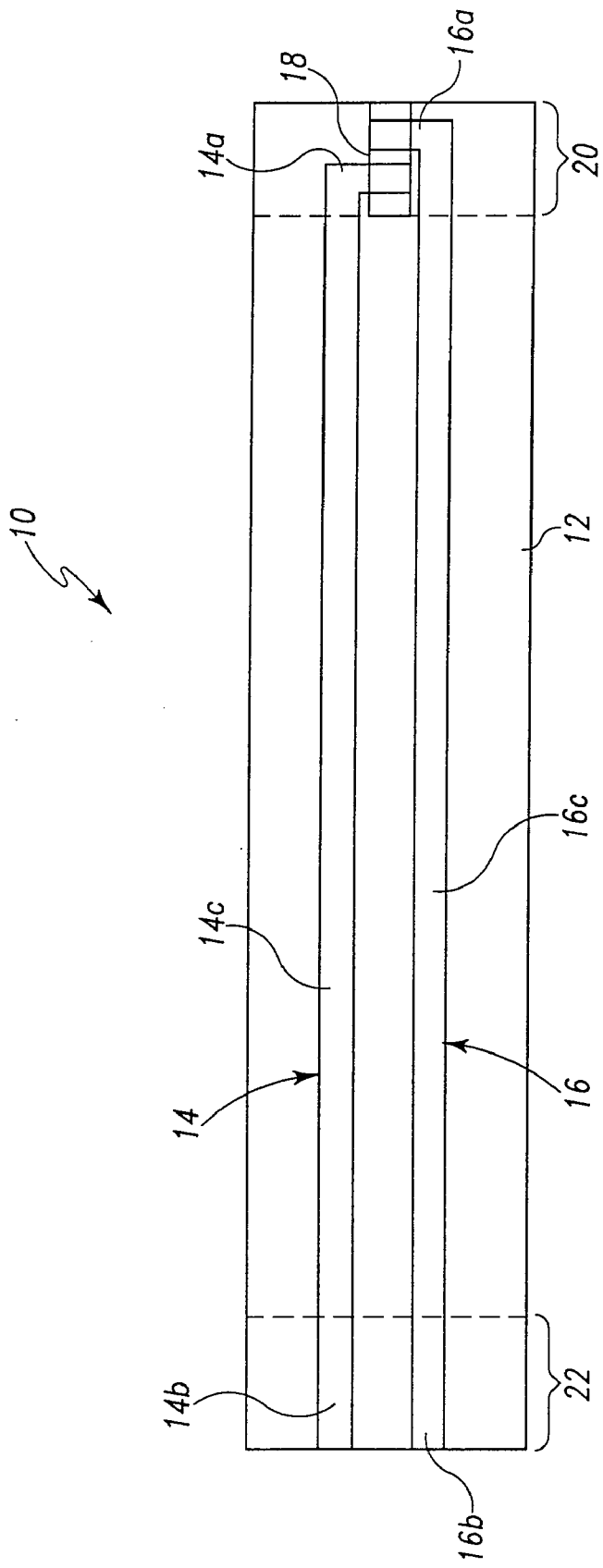
FIG. 1 is schematic plan view of a typical prior art test strip for use in measuring the concentration of an analyte of interest in a biological fluid.

For the purposes of promoting an understanding of the principles of the invention, reference will now be made to the embodiment illustrated in the drawings, and specific language will be used to describe that embodiment. It will nevertheless be understood that no limitation of the scope of the invention is intended. Alterations and modifications in the illustrated device, and further applications of the principles of the invention as illustrated therein, as would normally occur to one skilled in the art to which the invention relates are contemplated, are desired to be protected. In particular, although the invention is discussed in terms of a blood glucose meter, it is contemplated that the invention can be used with devices for measuring other analytes and other sample types. Such alternative embodiments require certain adaptations to the embodiments discussed herein that would be obvious to those skilled in the art.

Figure 2:
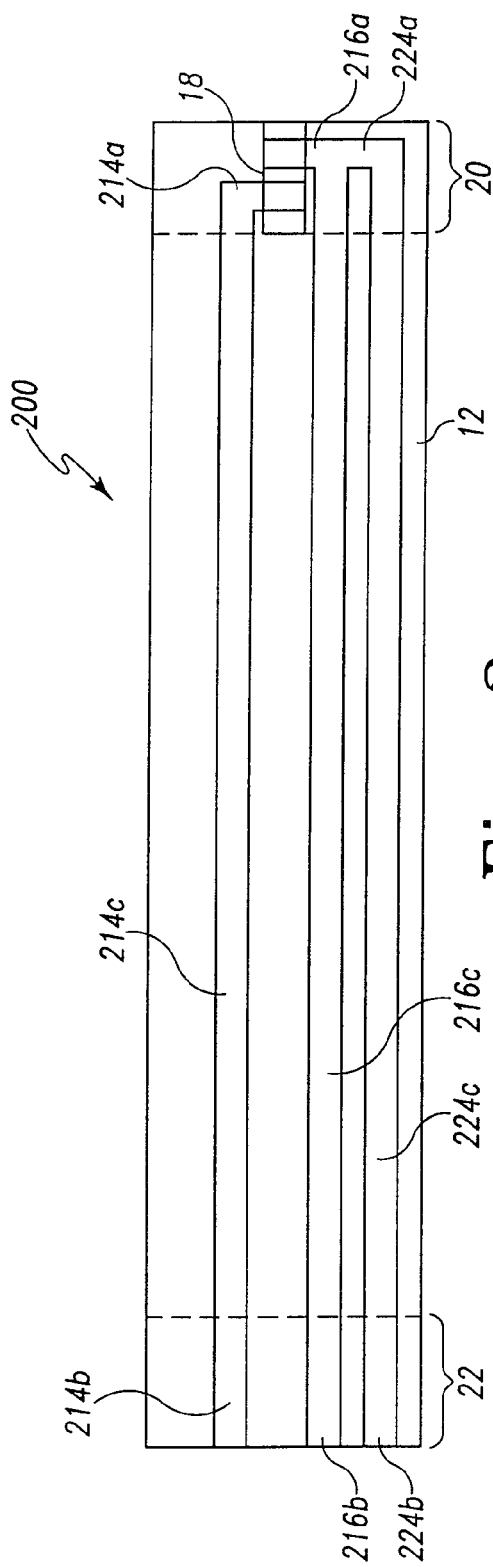
FIG. 2 is a schematic plan view of a first embodiment test strip according to the present invention.

Although the system and method of the present invention may be used with test strips having a wide variety of designs and made with a wide variety of construction techniques and processes, a first embodiment electrochemical test strip of the present invention is illustrated schematically in FIG. 2, and indicated generally at 200. Portions of test strip 200 which are substantially identical to those of test strip 10 are marked with like reference designators. Referring to FIG. 2, the test strip 200 comprises a bottom substrate 12 formed from an opaque piece of 350 μm thick polyester (such as Melinex 329 available from DuPont) coated on its top surface with a 50 nm conductive gold layer (for instance by sputtering or vapor deposition, by way of non-limiting example). Electrodes, connecting traces and contact pads therefor are then patterned in the conductive layer by a laser ablation process. The laser ablation process is performed by means of an excimer laser which passes through a chrome-on-quartz mask. The mask pattern causes parts of the laser field to be reflected while allowing other parts of the field to pass through, creating a pattern on the gold which is evaporated where contacted by the laser light. The laser ablation process is described in greater detail hereinbelow. For example, working 214a, counter 216a, and counter sense 224a electrodes may be formed as shown and coupled to respective measurement contact pads 214b, 216b and 224b by means of respective traces 214c, 216c and 224c. These contact pads 214b, 216b and 224b provide a conductive area upon the test strip 200 to be contacted by a connector contact of the test meter (not shown) once the test strip 200 is inserted into the test meter, as is well known in the art.

Figure 3:
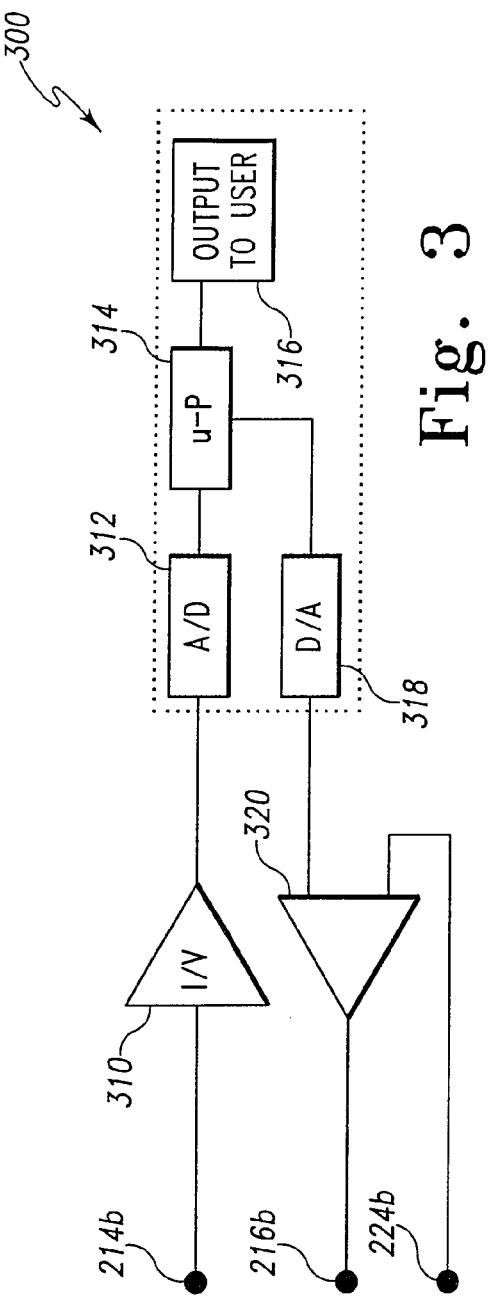
FIG. 3 is a schematic diagram of a first embodiment electronic test circuit for use with the first embodiment test strip of FIG. 2.

FIGS. 2 and 3 illustrate an embodiment of the present invention that improves upon the prior art test strip designs by allowing for compensation of parasitic I-R drop in the counter electrode line of the test strip. It will be appreciated that the test strip 200 of FIG. 2 is substantially identical to the prior art test strip 10 of FIG. 1, except for the addition of the counter sense electrode 224a, contact pad 224b, and trace 224c. Provision of the counter sense line 224 allows the test meter (as described hereinbelow) to compensate for parasitic resistance between the contact pads 216b,224b. Note that the embodiment of FIG. 2 when used with the circuit of FIG. 3 only compensates for the I-R drop on the counter electrode side of the test strip 200. Parasitic resistance on the working electrode side of the test strip 200 cannot be detected using this circuitry, although it could be replicated on the working electrode side if desired, as will be apparent to those skilled in the art with reference to the present diclosure. Further methods for compensating for parasitic resistance on both the working and counter sides of the test strip are presented hereinbelow. The counter sense line of FIG. 2 therefore allows the test meter to compensate for any parasitic resistance potential drop in the counter line 216, as explained in greater detail with respect to FIG. 3.

Referring now to FIG. 3, there is shown a schematic electrical circuit diagram of a first embodiment electrode compensation circuit (indicated generally at 300) housed within the test meter. As indicated, the circuit couples to contact pads 214b, 216b and 224b when the test strip 200 is inserted into the test meter. As will be appreciated by those skilled in the art, a voltage potential is applied to the counter electrode contact pad 216b, which will produce a current between the counter electrode 216a and the working electrode 214a that is proportional to the amount of analyte present in the biological sample applied to the reagent 18. The current from working electrode 214a is transmitted to working electrode contact pad 214b by means of working electrode trace 214c and provided to a current-to-voltage amplifier 310. The analog output voltage of amplifier 310 is converted to a digital signal by analog-to-digital converter (A/D) 312. This digital signal is then processed by microprocessor 314 according to a previously stored program in order to determine the concentration of analyte within the biological sample applied to the test strip 200. This concentration is displayed to the user by means of an appropriate output device 316, such as a liquid crystal display (LCD) screen.

Microprocessor 314 also outputs a digital signal indicative of the voltage potential to be applied to the counter electrode contact pad 216b. This digital signal is converted to an analog voltage signal by digital-to-analog converter (D/A) 318. The analog output of D/A 318 is applied to a first input of an operational amplifier 320. A second input of the operational amplifier 320 is coupled to counter sense electrode contact pad 224b. The output of operational amplifier 320 is coupled to the counter electrode contact pad 216b.

Operational amplifier 320 is connected in a voltage follower configuration, in which the amplifier will adjust its output (within its physical limits of operation) until the voltage appearing at its second input is equal to the commanded voltage appearing at its first input. The second input of operational amplifier 320 is a high impedance input, therefore substantially no current flows in counter sense line 224. Since substantially no current flows, any parasitic resistance in counter sense line 224 will not cause a potential drop, and the voltage appearing at the second input of operational amplifier 320 is substantially the same as the voltage at counter sense electrode 224a, which is in turn substantially the same as the voltage appearing at counter electrode 216a due to their close physical proximity. Operational amplifier 320 therefore acts to vary the voltage potential applied to the counter electrode contact pad 216b until the actual voltage potential appearing at the counter electrode 216a (as fed back over counter sense line 224) is equal to the voltage potential commanded by the microprocessor 314. Operational amplifier 320 therefore automatically compensates for any potential drop caused by the parasitic resistance in the counter electrode trace 216c, and the potential appearing at the counter electrode 216a is the desired potential. The calculation of the analyte concentration in the biological sample from the current produced by the working electrode is therefore made more accurate, since the voltage that produced the current is indeed the same voltage commanded by the microprocessor 314. Without the compensation for parasitic resistance voltage drops provided by the circuit 300, the microprocessor 314 would analyze the resulting current under the mistaken presumption that the commanded voltage was actually applied to the counter electrode 216a.

Many methods are available for preparing test strips having multiple electrodes, such as carbon ink printing, silver paste silk-screening, scribing metalized plastic, electroplating, chemical plating, and photo-chemical etching, by way of non-limiting example. One preferred method of preparing a test strip having additional electrode sense lines as described herein is by the use of laser ablation techniques. Examples of the use of these techniques in preparing electrodes for biosensors are described in U.S. patent application Ser. No. 09/866,030, "Biosensors with Laser Ablation Electrodes with a Continuous Coverlay Channel" filed May 25, 2001, and in U.S. patent application Ser. No. 09/411,940, entitled "Laser Defined Features for Patterned Laminates and Electrode," filed Oct. 4, 1999, both disclosures incorporated herein by reference. Laser ablation is particularly useful in preparing test strips according to the present invention because it allows conductive areas having extremely small feature sizes to be accurately manufactured in a repeatable manner. Laser ablation provides a means for adding the extra sense lines of the present invention to a test strip without increasing the size of the test strip.

It is desirable in the present invention to provide for the accurate placement of the electrical components relative to one another and to the overall biosensor. In a preferred embodiment, the relative placement of components is achieved, at least in part, by the use of broad field laser ablation that is performed through a mask or other device that has a precise pattern for the electrical components. This allows accurate positioning of adjacent edges, which is further enhanced by the close tolerances for the smoothness of the edges.

Figure 4:
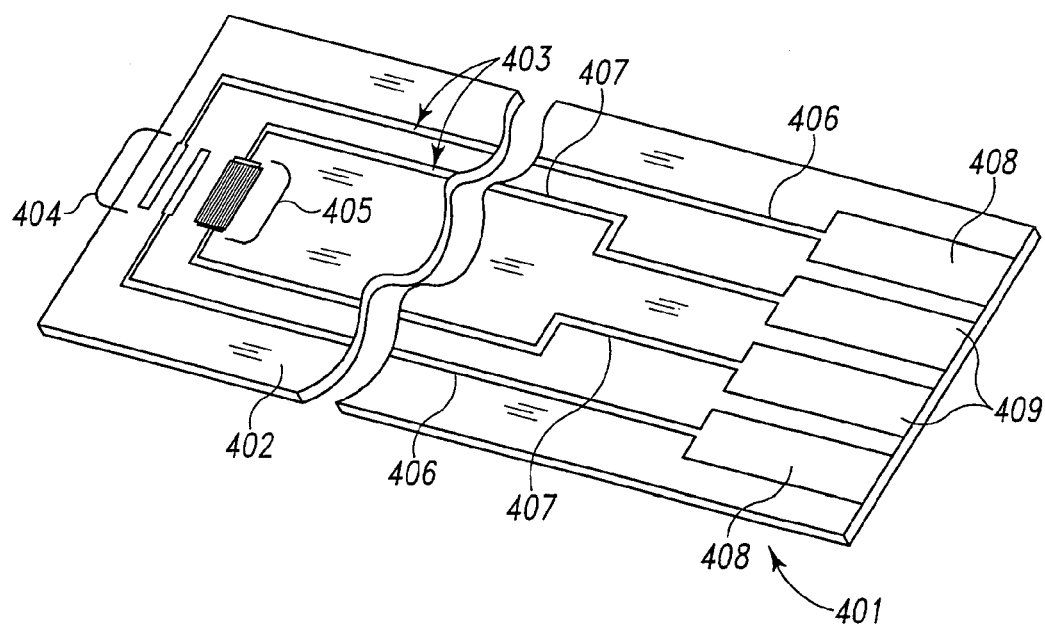
FIG. 4 is an exploded assembly view of a second typical test strip for use in measuring the concentration of an analyte of interest in a biological fluid.

FIG. 4 illustrates a simple biosensor 401 useful for illustrating the laser ablation process of the present invention, including a substrate 402 having formed thereon conductive material 403 defining electrode systems comprising a first electrode set 404 and a second electrode set 405, and corresponding traces 406, 407 and contact pads 408, 409, respectively. Note that the biosensor 401 is used herein for purposes of illustrating the laser ablation process, and that it is not shown as incorporating the sense lines of the present invention. The conductive material 403 may contain pure metals or alloys, or other materials, which are metallic conductors. Preferably, the conductive material is absorptive at the wavelength of the laser used to form the electrodes and of a thickness amenable to rapid and precise processing. Non-limiting examples include aluminum, carbon, copper, chromium, gold, indium tin oxide (ITO), palladium, platinum, silver, tin oxide/gold, titanium, mixtures thereof, and alloys or metallic compounds of these elements. Preferably, the conductive material includes noble metals or alloys or their oxides. Most preferably, the conductive material includes gold, palladium, aluminum, titanium, platinum, ITO and chromium. The conductive material ranges in thickness from about 10 nm to 80 nm, more preferably, 30 nm to 70 nm, and most preferably 50 nm. It is appreciated that the thickness of the conductive material depends upon the transmissive property of the material and other factors relating to use of the biosensor.

While not illustrated, it is appreciated that the resulting patterned conductive material can be coated or plated with additional metal layers. For example, the conductive material may be copper, which is then ablated with a laser into an electrode pattern; subsequently, the copper may be plated with a titanium/tungsten layer, and then a gold layer, to form the desired electrodes. Preferably, a single layer of conductive material is used, which lies on the base 402. Although not generally necessary, it is possible to enhance adhesion of the conductive material to the base, as is well known in the art, by using seed or ancillary layers such as chromium nickel or titanium. In preferred embodiments, biosensor 401 has a single layer of gold, palladium, platinum or ITO.

Figure 5:
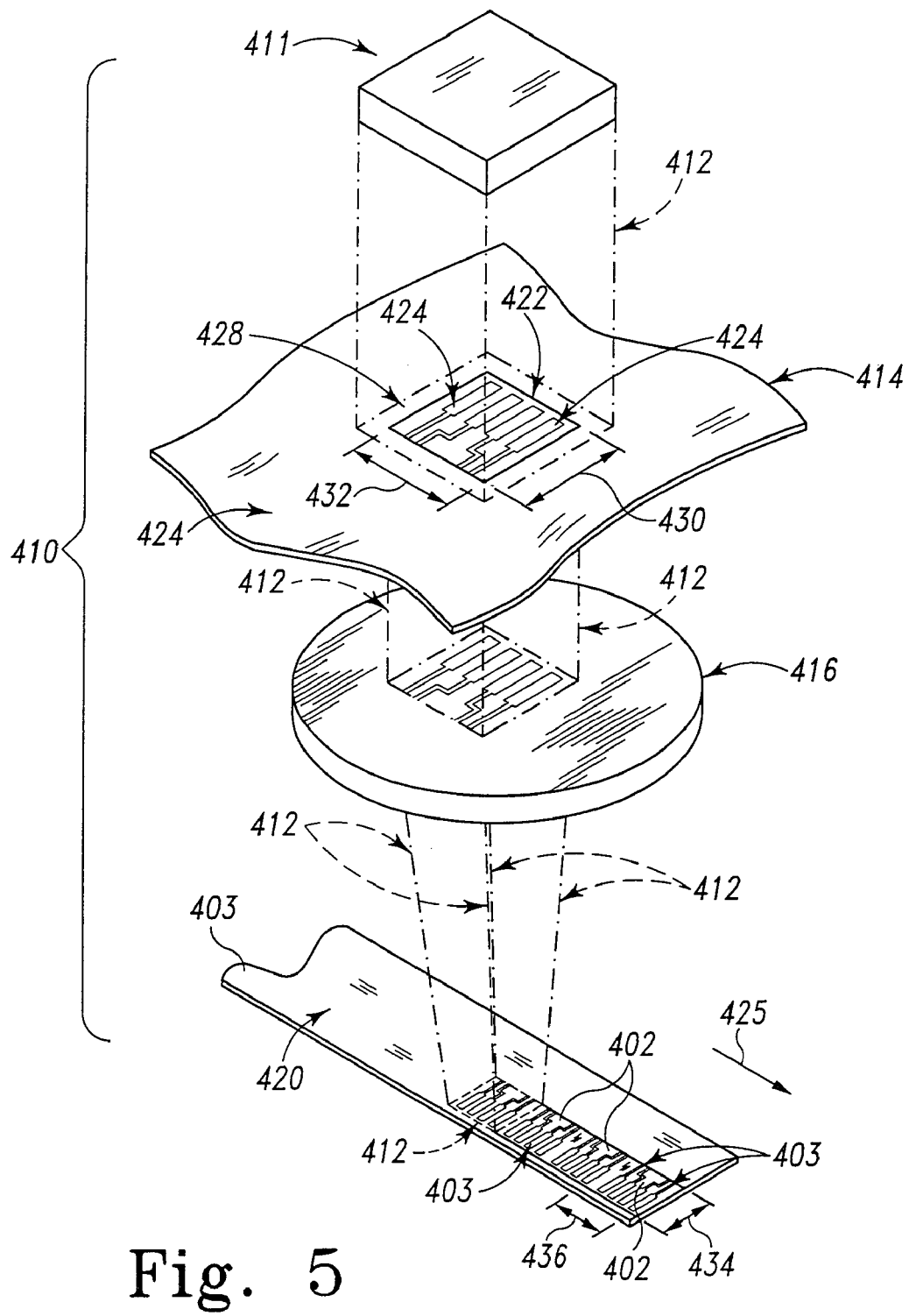
FIG. 5 illustrates a view of an ablation apparatus suitable for use with the present invention.
Figure 6:
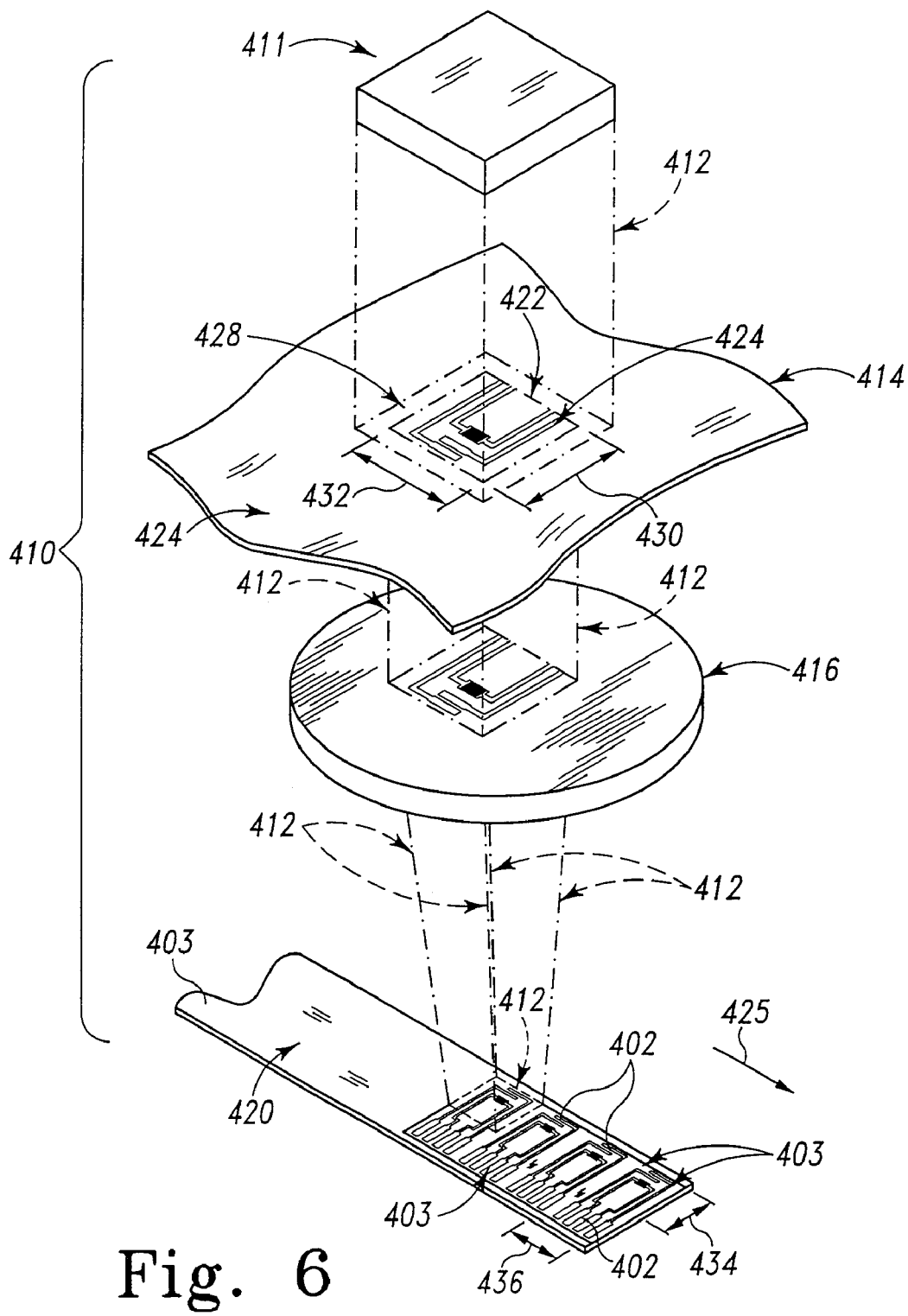
FIG. 6 is a view of the laser ablation apparatus of FIG. 5 showing a second mask.
Figure 7:
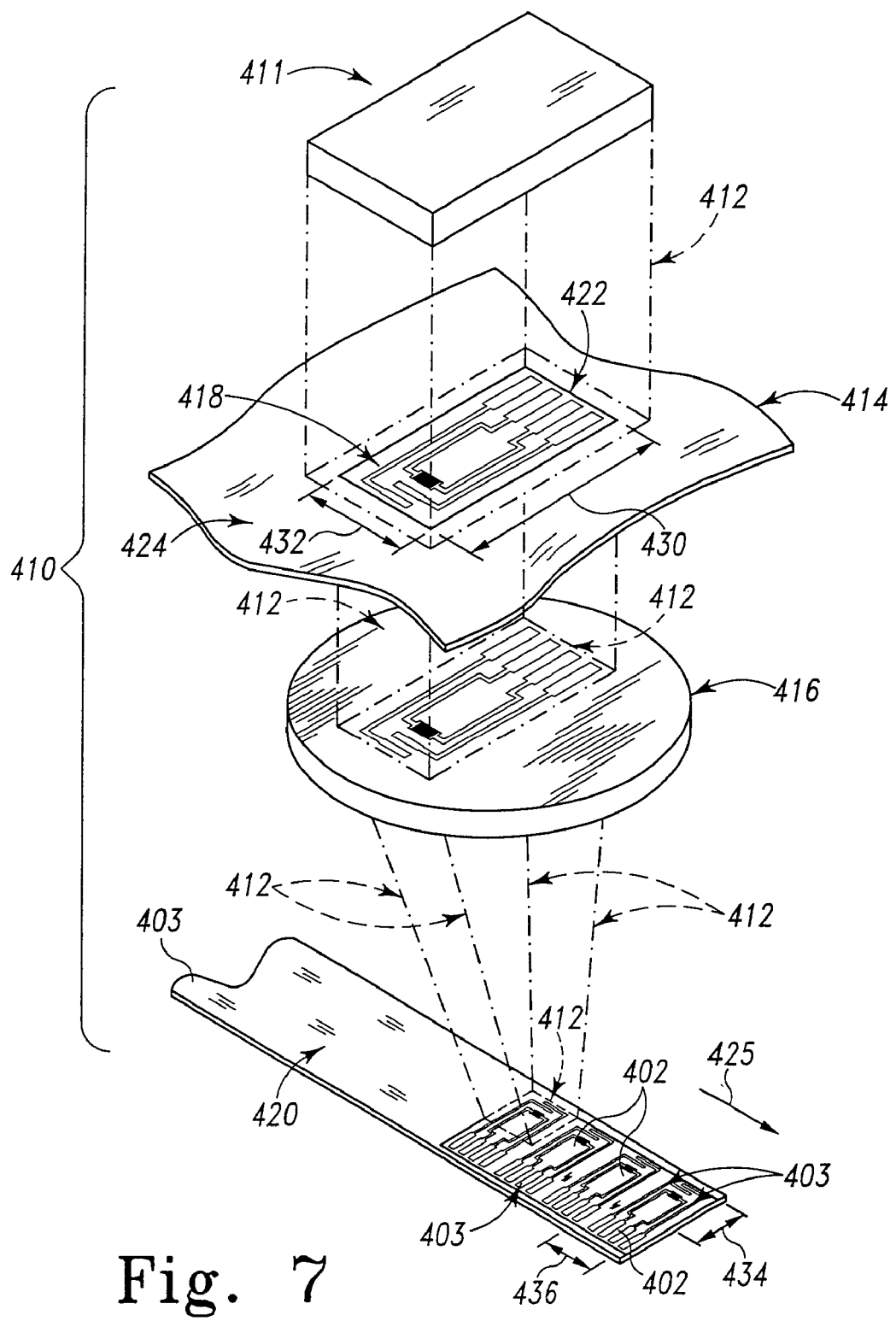
FIG. 7 is a view of an ablation apparatus suitable for use with the present invention.

Biosensor 401 is illustratively manufactured using two apparatuses 10, 10', shown in FIGS. 4,6 and 7, respectively. It is appreciated that unless otherwise described, the apparatuses 410, 410' operate in a similar manner. Referring first to FIG. 5, biosensor 401 is manufactured by feeding a roll of ribbon 420 having an 80 nm gold laminate, which is about 40 mm in width, into a custom fit broad field laser ablation apparatus 410. The apparatus 410 comprises a laser source 411 producing a beam of laser light 412, a chromium-plated quartz mask 414, and optics 416. It is appreciated that while the illustrated optics 416 is a single lens, optics 416 is preferably a variety of lenses that cooperate to make the light 412 in a pre-determined shape.

A non-limiting example of a suitable ablation apparatus 410 (FIGS. 5-6) is a customized MicrolineLaser 200-4 laser system commercially available from LPKF Laser Electronic GmbH, of Garbsen, Germany, which incorporates an LPX-400, LPX-300 or LPX-200 laser system commercially available from Lambda Physik AG, Gottingen, Germany and a chromium-plated quartz mask commercially available from International Phototool Company, Colorado Springs, Co.

For the MicrolineLaser 200-4 laser system (FIGS. 5-6), the laser source 411 is a LPX-200 KrF-UV-laser. It is appreciated, however, that higher wavelength UV lasers can be used in accordance with this disclosure. The laser source 411 works at 248 nm, with a pulse energy of 600 mJ, and a pulse repeat frequency of 50 Hz. The intensity of the laser beam 412 can be infinitely adjusted between 3% and 92% by a dielectric beam attenuator (not shown). The beam profile is 27×15 mm$^2$ (0.62 sq. inch) and the pulse duration 25 ns. The layout on the mask 414 is homogeneously projected by an optical elements beam expander, homogenizer, and field lens (not shown). The performance of the homogenizer has been determined by measuring the energy profile. The imaging optics 416 transfer the structures of the mask 414 onto the ribbon 420. The imaging ratio is 2:1 to allow a large area to be removed on the one hand, but to keep the energy density below the ablation point of the applied chromium mask on the other hand. While an imaging of 2:1 is illustrated, it is appreciated that the any number of alternative ratios are possible in accordance with this disclosure depending upon the desired design requirements. The ribbon 420 moves as shown by arrow 425 to allow a number of layout segments to be ablated in succession.

The positioning of the mask 414, movement of the ribbon 420, and laser energy are computer controlled. As shown in FIG. 5, the laser beam 412 is projected onto the ribbon 420 to be ablated. Light 412 passing through the clear areas or windows 418 of the mask 414 ablates the metal from the ribbon 420. Chromium coated areas 424 of the mask 414 blocks the laser light 412 and prevent ablation in those areas, resulting in a metallized structure on the ribbon 420 surface. Referring now to FIG. 6, a complete structure of electrical components may require additional ablation steps through a second mask 414'. It is appreciated that depending upon the optics and the size of the electrical component to be ablated, that only a single ablation step or greater than two ablation steps may be necessary in accordance with this disclosure. Further, it is appreciated that instead of multiple masks, that multiple fields may be formed on the same mask in accordance with this disclosure.

Specifically, a second non-limiting example of a suitable ablation apparatus 410' (FIG. 7) is a customized laser system commercially available from LPKF Laser Electronic GmbH, of Garbsen, Germany, which incorporates a Lambda STEEL (Stable energy eximer laser) laser system commercially available from Lambda Physik AG, Gottingen, Germany and a chromium-plated quartz mask commercially available from International Phototool Company, Colorado Springs, Co. The laser system features up to 1000 mJ pulse energy at a wavelength of 308 nm. Further, the laser system has a frequency of 100 Hz. The apparatus 410' may be formed to produce biosensors with two passes as shown in FIGS. 5 and 6, but preferably its optics permit the formation of a 10×40 mm pattern in a 25 ns single pass.

While not wishing to be bound to a specific theory, it is believed that the laser pulse or beam 412 that passes through the mask 414, 414', 414" is absorbed within less than 1 µm of the surface 402 on the ribbon 420. The photons of the beam 412 have an energy sufficient to cause photo-dissociation and the rapid breaking of chemical bonds at the metal/polymer interface. It is believed that this rapid chemical bond breaking causes a sudden pressure increase within the absorption region and forces material (metal film 403) to be ejected from the polymer base surface. Since typical pulse durations are around 20-25 nanoseconds, the interaction with the material occurs very rapidly and thermal damage to edges of the conductive material 403 and surrounding structures is minimized. The resulting edges of the electrical components have high edge quality and accurate placement as contemplated by the present invention.

Fluence energies used to remove or ablate metals from the ribbon 420 are dependent upon the material from which the ribbon 420 is formed, adhesion of the metal film to the base material, the thickness of the metal film, and possibly the process used to place the film on the base material, i.e. supporting and vapor deposition. Fluence levels for gold on KALADEX® range from about 50 to about 90 mJ/cm$^2$, on polyimide about 100 to about 120 mJ/cm$^2$, and on MELINEX® about 60 to about 120 mJ/cm$^2$. It is understood that fluence levels less than or greater than the above mentioned can be appropriate for other base materials in accordance with the disclosure.

Patterning of areas of the ribbon 420 is achieved by using the masks 414, 414'. Each mask 414, 414' illustratively includes a mask field 422 containing a precise two-dimensional illustration of a pre-determined portion of the electrode component patterns to be formed. FIG. 5 illustrates the mask field 422 including contact pads and a portion of traces. As shown in FIG. 6, the second mask 414' contains a second corresponding portion of the traces and the electrode patterns containing fingers. As previously described, it is appreciated that depending upon the size of the area to be ablated, the mask 414 can contain a complete illustration of the electrode patterns (FIG. 7), or portions of patterns different from those illustrated in FIGS. 5 and 6 in accordance with this disclosure. Preferably, it is contemplated that in one aspect of the present invention, the entire pattern of the electrical components on the test strip are laser ablated at one time, i.e., the broad field encompasses the entire size of the test strip (FIG. 7). In the alternative, and as illustrated in FIGS. 5 and 6, portions of the entire biosensor are done successively.

While mask 414 will be discussed hereafter, it is appreciated that unless indicated otherwise, the discussion will apply to masks 414', 414" as well. Referring to FIG. 5, areas 424 of the mask field 422 protected by the chrome will block the projection of the laser beam 412 to the ribbon 420. Clear areas or windows 418 in the mask field 422 allow the laser beam 412 to pass through the mask 414 and to impact predetermined areas of the ribbon 420. As shown in FIG. 5, the clear area 418 of the mask field 422 corresponds to the areas of the ribbon 420 from which the conductive material 403 is to be removed.

Further, the mask field 422 has a length shown by line 430 and a width as shown by line 432. Given the imaging ratio of 2:1 of the LPX-200, it is appreciated that the length 30 of the mask is two times the length of a length 434 of the resulting pattern and the width 432 of the mask is two times the width of a width 436 of the resulting pattern on ribbon 420. The optics 416 reduces the size of laser beam 412 that strikes the ribbon 420. It is appreciated that the relative dimensions of the mask field 422 and the resulting pattern can vary in accordance with this disclosure. Mask 414' (FIG. 6) is used to complete the two-dimensional illustration of the electrical components.

Continuing to refer to FIG. 5, in the laser ablation apparatus 410 the excimer laser source 411 emits beam 412, which passes through the chrome-on-quartz mask 414. The mask field 422 causes parts of the laser beam 412 to be reflected while allowing other parts of the beam to pass through, creating a pattern on the gold film where impacted by the laser beam 412. It is appreciated that ribbon 420 can be stationary relative to apparatus 410 or move continuously on a roll through apparatus 410. Accordingly, non-limiting rates of movement of the ribbon 420 can be from about 0 m/min to about 100 m/min, more preferably about 30 m/min to about 60 m/min. It is appreciated that the rate of movement of the ribbon 420 is limited only by the apparatus 410 selected and may well exceed 100 m/min depending upon the pulse duration of the laser source 411 in accordance with the present disclosure.

Once the pattern of the mask 414 is created on the ribbon 420, the ribbon is rewound and fed through the apparatus 410 again, with mask 414' (FIG. 6). It is appreciated, that alternatively, laser apparatus 410 could be positioned in series in accordance with this disclosure. Thus, by using masks 414, 414', large areas of the ribbon 420 can be patterned using step-and-repeat processes involving multiple mask fields 422 in the same mask area to enable the economical creation of intricate electrode patterns and other electrical components on a substrate of the base, the precise edges of the electrode components, and the removal of greater amounts of the metallic film from the base material.

Figure 8:
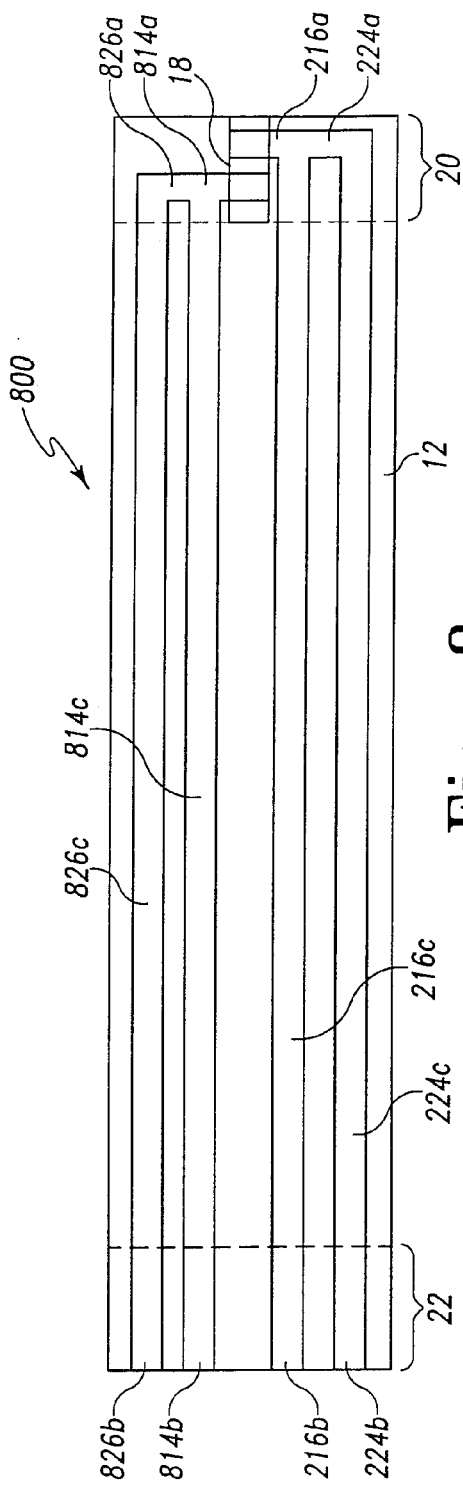
FIG. 8 is a schematic plan view of a second embodiment test strip according to the present invention.
Figure 9:
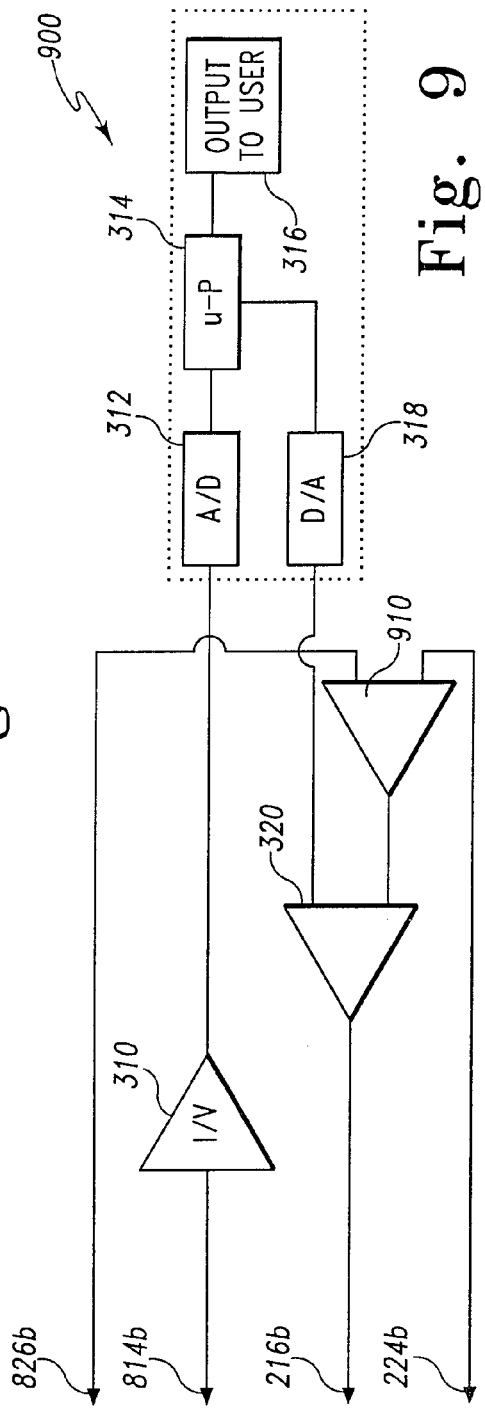
FIG. 9 is a schematic diagram of a second embodiment electronic test circuit for use with the second embodiment test strip of FIG. 8.

The second embodiment of the present invention illustrated in FIGS. 8 and 9 improve upon the prior art by providing for I-R drop compensation of both the working and counter electrode leads on the test strip. Referring now to FIG. 8, there is schematically illustrated a second embodiment test strip configuration of the present invention, indicated generally at 800. The test strip 800 comprises a bottom substrate 12 coated on its top surface with a 50 nm conductive gold layer (for instance by sputtering or vapor deposition, by way of non-limiting example). Electrodes, connecting traces and contact pads therefor are then patterned in the conductive layer by a laser ablation process as described hereinabove. For example, working 814a, working sense 826a, counter 216a, and counter sense 224a electrodes may be formed as shown and coupled to respective measurement contact pads 814b, 826b, 216b and 224b by means of respective traces 814c, 826c, 216c and 224c. These contact pads 814b, 826b, 216b and 224b provide a conductive area upon the test strip 800 to be contacted by a connector contact of the test meter (not shown) once the test strip 800 is inserted into the test meter.

It will be appreciated that the test strip 800 of FIG. 8 is substantially identical to the first embodiment test strip 200 of FIG. 2, except for the addition of the working sense electrode 826a, contact pad 826b, and trace 826c. Provision of the working sense line 826 allows the test meter to compensate for any I-R drop caused by the contact resistance of the connections to the contact pads 814b and 216b, and to compensate for the trace resistance of traces 814c and 216c.

Referring now to FIG. 9, there is shown a schematic electrical circuit diagram of a second embodiment electrode compensation circuit (indicated generally at 900) housed within the test meter. As indicated, the circuit couples to contact pads 826b, 814b, 216b and 224b when the test strip 800 is inserted into the test meter. As will be appreciated by those skilled in the art, a voltage potential is applied to the counter electrode contact pad 216b, which will produce a current between the counter electrode 216a and the working electrode 814a that is proportional to the amount of analyte present in the biological sample applied to the reagent 18. The current from working electrode 814a is transmitted by working electrode trace 814c to working electrode contact pad 814b and provided to current-to-voltage amplifier 310. The analog output voltage of amplifier 310 is converted to a digital signal by A/D 312. This digital signal is then processed by microprocessor 314 according to a previously stored program in order to determine the concentration of the analyte of interest within the biological sample applied to the test strip 800. This concentration is displayed to the user by means of LCD output device 316.

Microprocessor 314 also outputs a digital signal indicative of the voltage potential to be applied to the counter electrode contact pad 216b. This digital signal is converted to an analog voltage signal by D/A 318. The analog output of D/A 318 is applied to a first input of an operational amplifier 320. A second input of the operational amplifier 320 is coupled to an output of operational amplifier 910. Operational amplifier 910 is connected in a difference amplifier configuration using an instrumentation amplifier. A first input of operational amplifier 910 is coupled to working sense electrode contact pad 826b, while a second input of operational amplifier 910 is coupled to counter sense electrode contact pad 224b. The output of operational amplifier 320 is coupled to the counter electrode contact pad 216b.

Operational amplifier 320 is connected in a voltage follower configuration, in which the amplifier will adjust its output (within its physical limits of operation) until the voltage appearing at its second input is equal to the commanded voltage appearing at its first input. Both inputs of operational amplifier 910 are high impedance inputs, therefore substantially no current flows in counter sense line 224 or working sense line 826. Since substantially no current flows, any parasitic resistance in counter sense line 224 or working sense line 826 will not cause a potential drop, and the voltage appearing across the inputs of operational amplifier 910 is substantially the same as the voltage across the measurement cell (i.e. across counter electrode 216a and working electrode 814a). Because operational amplifier 910 is connected in a difference amplifier configuration, its output represents the voltage across the measurement cell.

Operational amplifier 320 will therefore act to vary its output (i.e. the voltage potential applied to the counter electrode contact pad 216b) until the actual voltage potential appearing across the measurement cell is equal to the voltage potential commanded by the microprocessor 314. Operational amplifier 320 therefore automatically compensates for any potential drop caused by the parasitic resistance in the counter electrode trace 216c, counter electrode contact 216b, working electrode trace 814c, and working electrode contact 814b, and therefore the potential appearing across the measurement cell is the desired potential. The calculation of the analyte concentration in the biological sample from the current produced by the working electrode is therefore made more accurate.

Figure 10:
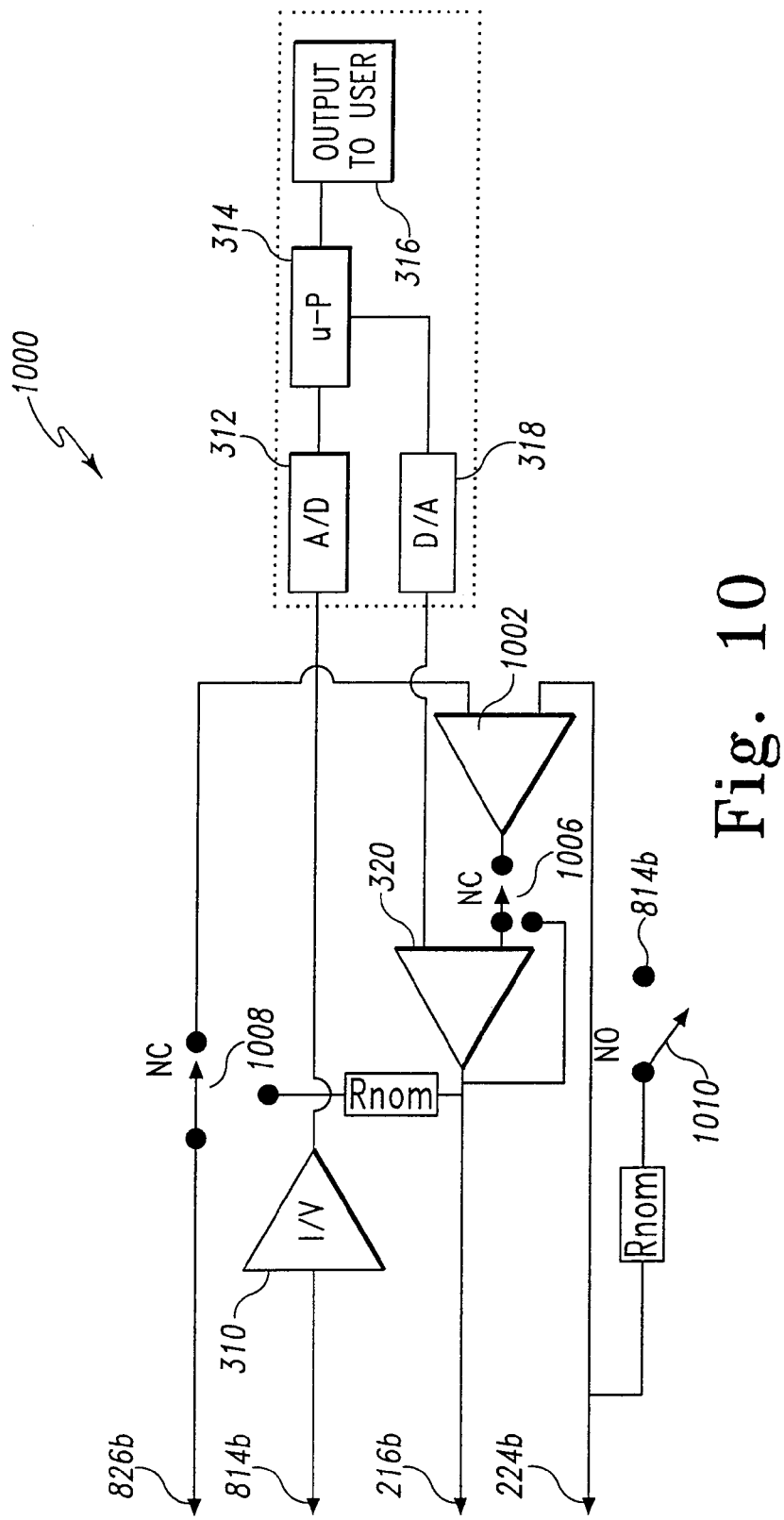
FIG. 10 is a schematic diagram of a third embodiment electronic test circuit for use with the second embodiment test strip of FIG. 8.

FIG. 10, in conjunction with FIG. 8, illustrates a third embodiment of the present invention that improves over the prior art by providing I-R drop compensation for both the working and counter electrode lines, as well as providing verification that the resistance of both the working and counter electrode lines is not above a predetermined threshold in order to assure that the test meter is able to compensate for the I-R drops. Referring now to FIG. 10, there is shown a schematic electrical circuit diagram of a third embodiment electrode compensation circuit (indicated generally at 1000) housed within the test meter. The electrode compensation circuit 1000 works with the test strip 800 of FIG. 8. As indicated, the circuit couples to contact pads 826b, 814b, 216b and 224b when the test strip 800 is inserted into the test meter. As will be appreciated by those skilled in the art, a voltage potential is applied to the counter electrode contact pad 216b, which will produce a current between the counter electrode 216a and the working electrode 814a that is proportional to the amount of analyte present in the biological sample applied to the reagent 18. The current from working electrode 814a is transmitted to working electrode contact pad 814b by working electrode trace 814c and provided to current-to-voltage amplifier 310. The output of current-to-voltage amplifier 310 is applied to the input of instrumentation amplifier 1002 which is configured as a buffer having unity gain when switch 1004 in the closed position. The analog output voltage of amplifier 1002 is converted to a digital signal by A/D 312. This digital signal is then processed by microprocessor 314 according to a previously stored program in order to determine the concentration of analyte within the biological sample applied to the test strip 800. This concentration is displayed to the user by means of LCD output device 316.

Microprocessor 314 also outputs a digital signal indicative of the voltage potential to be applied to the counter electrode contact pad 216b. This digital signal is converted to an analog voltage signal by D/A 318. The analog output of D/A 318 is applied to the input of an operational amplifier 320 that is configured as a voltage follower when switch 1006 is in the position shown. The output of operational amplifier 320 is coupled to the counter electrode contact pad 216b, which will allow measurement of a biological fluid sample applied to the reagent 18. Furthermore, with switches 1006, 1008 and 1010 positioned as illustrated in FIG. 10, the circuit is configured as shown in FIG. 9 and may be used to automatically compensate for parasitic and contact resistance as described hereinabove with respect to FIG. 9.

In order to measure the amount of parasitic resistance in the counter electrode line 216, switch 1008 is placed in the position shown in FIG. 10, switch 1006 is placed in the position opposite that shown in FIG. 10, while switch 1010 is closed. The operational amplifier 320 therefore acts as a buffer with unity gain and applies a voltage potential to counter electrode contact pad 216b through a known resistance $R_{nom}$. This resistance causes a current to flow in the counter electrode line 216 and the counter sense line 224 that is sensed by current-to-voltage amplifier 310, which is now coupled to the current sense line through switch 1010. The output of current-to-voltage amplifier 310 is provided to the microprocessor 314 through A/D 312. Because the value of $R_{nom}$ is known, the microprocessor 314 can calculate the value of any parasitic resistance in the counter sense line 224 and the counter electrode line 216. This parasitic resistance value can be compared to a predetermined threshold stored in the test meter to determine if physical damage has occurred to the test strip 800 or if nonconductive buildup is present on the contact pads to such an extent that the test strip 800 cannot be reliably used to perform a test. In such situations, the test meter may be programmed to inform the user that an alternate test strip should be inserted into the test meter before proceeding with the test.

In order to measure the amount of parasitic resistance in the working electrode line 814, switches 1006 and 1008 are placed in the position opposite that shown in FIG. 10, while switch 1010 is opened. The operational amplifier 320 therefore acts as a buffer with unity gain and applies a voltage potential to working sense contact pad 826b through a known resistance $R_{nom}$. This resistance causes a current to flow in the working sense line 826 and the working electrode line 814 that is sensed by current-to-voltage amplifier 310. The output of current-to-voltage amplifier 310 is provided to the microprocessor 314 through A/D 312. Because the value of $R_{nom}$ is known, the microprocessor 314 can calculate the value of any parasitic resistance in the working sense line 826 and the working electrode line 814. This parasitic resistance value can be compared to a predetermined threshold stored in the test meter to determine if physical damage has occurred to the test strip 800 or if nonconductive buildup is present on the contact pads to such an extent that the test strip 800 cannot be reliably used to perform a test. In such situations, the test meter may be programmed to inform the user that an alternate test strip should be inserted into the test meter before proceeding with the test.

All publications, prior applications, and other documents cited herein are hereby incorporated by reference in their entirety as if each had been individually incorporated by reference and fully set forth.

While the invention has been illustrated and described in detail in the drawings and foregoing description, the description is to be considered as illustrative and not restrictive in character. Only the preferred embodiment, and certain other embodiments deemed helpful in further explaining how to make or use the preferred embodiment, have been shown. All changes and modifications that come within the spirit of the invention are desired to be protected.

What is claimed:

1. A biosensor system, comprising:
    a biosensor test strip, comprising
        a first measurement electrode;
        a first conductive trace operatively coupled to the first measurement electrode; and
        a second conductive trace operatively coupled to the first measurement electrode;
    a test meter coupled to the biosensor test strip, the test meter comprising:
        a reference voltage source operably coupled to the first conductive trace;
        a known resistance having a first resistor end and a second resistor end, the first resistor end being operably coupled to the second conductive trace; and
        a current measurement device having an input coupled to the second resistor end;
        wherein application of the reference voltage causes a current to flow through the first conductive trace, the known resistance, and the second conductive trace; and
        wherein measurement of the current allows a parasitic resistance of the first and second conductive traces to be calculated.

2. The biosensor system of claim 1, wherein the current measurement device comprises:
    a current-to-voltage amplifier having an amplifier output;
    an analog-to-digital converter having a converter input and a converter output, the converter input being operably coupled to the amplifier output; and
    a computing device having a device input operably coupled to the converter output.

3. A biosensor system, comprising:
    a biosensor test strip, comprising
        a first measurement electrode;
        a first conductive trace operatively coupled to the first measurement electrode; and
        a second conductive trace operatively coupled to the first measurement electrode;
    a test meter coupled to the biosensor test strip, the test meter comprising:
        a reference voltage source having a voltage output;
        a known resistance having a first resistor end and a second resistor end, the first resistor end being operably coupled to the voltage output and the second resistor end being operably coupled to the first conductive trace; and
        a current measurement device having an input coupled to the second conductive trace;

wherein application of the reference voltage causes a current to flow through the known resistance, the first conductive trace, and the second conductive trace; and wherein measurement of the current allows a parasitic resistance of the first and second conductive traces to be calculated.

4. The biosensor system of claim 3, wherein the current measurement device comprises:

a current-to-voltage amplifier having an amplifier output;

an analog-to-digital converter having a converter input and a converter output, the converter input being operably coupled to the amplifier output; and a computing device having a device input operably coupled to the converter output.

* * * * *